United States Patent [19]

Elliott et al.

[11] Patent Number: 4,745,114
[45] Date of Patent: May 17, 1988

[54] BENZOPYRAN FUNGICIDAL COMPOSITIONS AND USE

[75] Inventors: Alison Elliott, Nr Reading; Vivienne Anthony, Maidenhead, both of United Kingdom

[73] Assignee: Imperial Chemical Industries PLC, London, England

[21] Appl. No.: 869,568

[22] Filed: Jun. 2, 1986

[30] Foreign Application Priority Data

Jun. 18, 1985 [GB] United Kingdom ................. 8515389

[51] Int. Cl.$^4$ ............................................. A01N 43/84
[52] U.S. Cl. ................................. 514/233.5; 514/320; 514/456; 544/151; 546/196; 424/45; 71/88; 71/92; 71/94
[58] Field of Search ................ 514/227, 239; 544/151; 424/45

[56] References Cited

U.S. PATENT DOCUMENTS 3,156,688 11/1964 Zaugg et al. .................... 544/151

OTHER PUBLICATIONS

Gupta et al., Chemical Abstracts, vol. 98, (1983), No. 16543p.

Primary Examiner—Robert W. Ramsuer
Attorney, Agent, or Firm—Cushman, Darby & Cushman

[57] ABSTRACT

The invention provides fungicidal compositions comprising as an active ingredient a compound having the general formula (I):

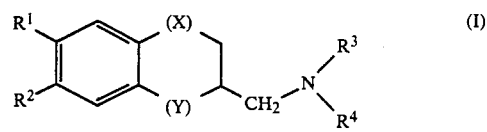

or a stereoisomer thereof, wherein X is a methylene group and Y is an oxygen atom, or X is an oxygen atom and Y is a methylene or CHOH group; $R^1$ and $R^2$, which may be the same or different, are hydrogen or halogen atoms, or alkyl, alkenyl, alkynyl, alkoxy, haloalkyl, or haloalkoxy groups; $R^3$ and $R^4$, which may be the same or different, are alkyl groups containing from 1 to 8 carbon atoms, or $-NR^3R^4$ is a 5- or 6-membered heterocyclic ring, optionally substituted by alkyl, aryl, aralkyl, hydroxy, alkoxy or aryloxy groups; or an acid addition salt of such a compound.

5 Claims, No Drawings

BENZOPYRAN FUNGICIDAL COMPOSITIONS AND USE

This invention relates to fungicidal compositions containing tertiary amine compounds and to methods of using them to combat fungi, especially fungal infections in plants; the invention also relates to certain of those compounds which are novel per se.

The invention provides fungicidal compositions comprising as an active ingredient a compound having the general formula (I):

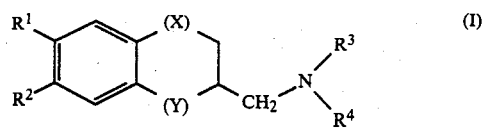

or a stereoisomer thereof, wherein X is a methylene group and Y is an oxygen atom, or X is an oxygen atom and Y is a methylene or CHOH group; $R^1$ and $R^2$, which may be the same or different, are hydrogen or halogen atoms, or alkyl, alkenyl, alkynyl, alkoxy, haloalkyl, or haloalkoxy groups; $R^3$ and $R^4$, which may be the same or different, are alkyl groups containing from 1 to 8 carbon atoms, or $-NR^3R^4$ is a 5- or 6-membered heterocyclic ring, optionally substituted by alkyl, aryl, aralkyl, hydroxy, alkoxy or aryloxy groups; or an acid addition salt of such a compound.

The compounds incorporated in the compositions of the invention are sometimes obtained in the form of mixtures of geometrical isomers. However, these and mixtures of optical isomers can be separated into individual isomers by methods known in the art, and compositions incorporating such individual isomers form part of the present invention.

Alkyl and alkoxy groups for $R^1$ and/or $R^2$ may be in the form of straight or branched chains and preferably contain 1 to 4 carbon atoms: excamples are methyl, ethyl, propyl (n- or iso-propyl) and butyl (n, sec, iso- or tert-butyl).

Alkenyl and alkynyl groups may contain up to 6 carbon atoms.

Halogen atoms may be fluorine, chlorine or bromine.

Preferred compounds are those having $-NR^3R^4$ as a 5- or 6-membered heterocyclic ring, such as a piperidine, pyrrolidine, morpholine, piperazine or nortropane ring, or a substituted derivative thereof. Especially preferred ring systems are those of piperidine, 4-phenyl-piperidine and 2,6-dimethylmorpholine.

The salts of the compounds can be salts with inorganic or organic acids eg. hydrochloric, nitric, sulphuric, acetic, 4-toluene-sulphonic or oxalic acid.

Certain compounds falling within the general formula (I) where X is oxygen and Y is a methylene group are already known from the paper by Gupta, Pratap, Prasad and Anand in Indian Journal of Chemistry, Vol. 21B, April 1982, pages 344–347. These include, for example, compounds in which the group $-NR^3R^4$ is a piperidine or substituted piperazine ring. The compounds in question are, however, all described with reference to their central muscle relaxant activity and there is no disclosure of the possession by any of them of fungicidal properties.

Examples of compounds conforming to formula (I) which may be incorporated in compositions according to the present invention are shown in Table I; nmr data for certain of these compounds are given in Table II.

TABLE I

| NO. | $R^1$ | $R^2$ | X | Y | $-NR^3R^4$ | Melting Point °C. | M+ |
|---|---|---|---|---|---|---|---|
| 1 | H | H | $CH_2$ | O | $-N$ morpholine with two $CH_3$ groups (2,6-dimethylmorpholine) | oil | 261 |
| 2 | H | H | $CH_2$ | O | $-N$ piperidine | | |
| 3 | H | H | $CH_2$ | O | $-N$ 3,5-dimethylpiperidine | oil | 259 |
| 4 | H | H | $CH_2$ | O | $-N$ 4-phenylpiperidine | oil | 307 |

TABLE I-continued $$R^1, R^2 \text{ substituted benzene with (X) and (Y) positions, } CH_2NR^3R^4$$

| NO. | R¹ | R² | X | Y | —NR³R⁴ | Melting Point °C. | M+ |
|-----|-----|-----|-----|-----|--------|-------------------|-----|
| 5 | H | H | CH₂ | O | 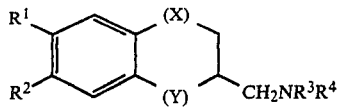 4-hydroxy-4-phenylpiperidinyl | oil | 323 |
| 6 | CH₃ | H | CH₂ | O | 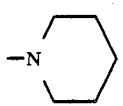 piperidinyl | | |
| 7 | CH₃ | H | CH₂ | O | 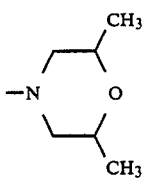 2,6-dimethylmorpholinyl | | |
| 8 | CH₃ | H | CH₂ | O | 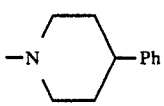 4-phenylpiperidinyl | | |
| 9 | OCH₃ | H | CH₂ | O | 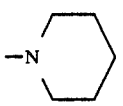 piperidinyl | | |
| 10 | OCH₃ | H | CH₂ | O | 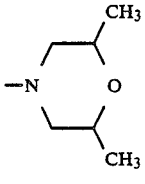 2,6-dimethylmorpholinyl | | |
| 11 | OCH₃ | H | CH₂ | O | 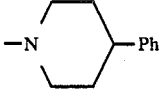 4-phenylpiperidinyl | | |
| 12 | C₂H₅ | H | CH₂ | O | 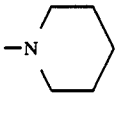 piperidinyl | | |
| 13 | C₂H₅ | H | CH₂ | O | 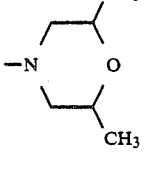 2,6-dimethylmorpholinyl | | |
| 14 | C₂H₅ | H | CH₂ | O | 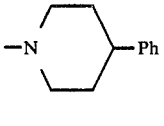 4-phenylpiperidinyl | | |

TABLE I-continued $$R^1 \text{-benzene-} R^2, (X), (Y), CH_2NR^3R^4$$

| NO. | R¹ | R² | X | Y | —NR³R⁴ | Melting Point °C. | M+ |
|---|---|---|---|---|---|---|---|
| 15 | i-C₃H₇ | H | CH₂ | O | 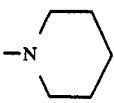 piperidine | | |
| 16 | i-C₃H₇ | H | CH₂ | O | 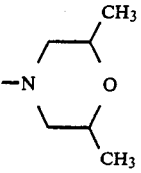 2,6-dimethylmorpholine | | |
| 17 | i-C₃H₇ | H | CH₂ | O | 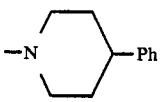 4-phenylpiperidine | | |
| 18 | t-C₄H₉ | H | CH₂ | O | 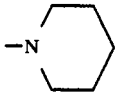 piperidine | | |
| 19 | t-C₄H₉ | H | CH₂ | O | 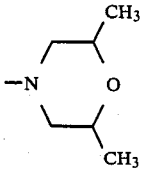 2,6-dimethylmorpholine | | |
| 20 | t-C₄H₉ | H | CH₂ | O | 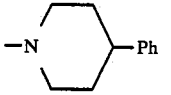 4-phenylpiperidine | | |
| 21 | t-C₄H₉ | H | CH₂ | O | 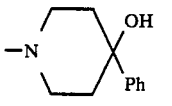 4-hydroxy-4-phenylpiperidine | | |
| 22 | t-C₄H₉ | H | CH₂ | O | 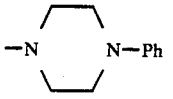 4-phenylpiperazine | | |
| 23 | t-C₄H₉ | H | CH₂ | O | —N(C₂H₅)₂ | | |
| 24 | H | OCH₃ | CH₂ | O | 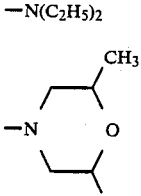 2,6-dimethylmorpholine | | |
| 25 | H | OCH₃ | CH₂ | O | 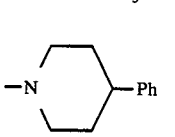 4-phenylpiperidine | | |

TABLE I-continued $$\underset{R^2}{\overset{R^1}{\bigg|}}\underset{(Y)}{\overset{(X)}{\bigg|}}CH_2NR^3R^4$$

| NO. | R¹ | R² | X | Y | —NR³R⁴ | Melting Point °C. | M+ |
|---|---|---|---|---|---|---|---|
| 26 | H | t-C₄H₉ | CH₂ | O | piperidine | | |
| 27 | H | t-C₄H₉ | CH₂ | O | 2,6-dimethylmorpholine | | |
| 28 | H | H | O | CHOH trans | 4-phenylpiperidine | oil | 395 (SiMe₃ derivative) |
| 29 | H | H | O | CHOH cis | 4-phenylpiperidine | oil | 395 (SiMe₃ derivative) |
| 30 | H | H | O | CH₂ | 4-phenylpiperidine | oil | 307 |
| 31 | H | H | O | CH₂ | piperidine | | |
| 32 | H | H | O | CH₂ | 2,6-dimethylmorpholine | | |
| 33 | H | H | O | CH₂ | 4-hydroxy-4-phenylpiperidine | | |
| 34 | H | CH₃ | O | CH₂ | piperidine | | |
| 35 | H | CH₃ | O | CH₂ | 2,6-dimethylmorpholine | | |

TABLE I-continued $$R^1, R^2 \text{ on benzene ring fused to ring containing (X) and (Y), with CH}_2NR^3R^4 \text{ substituent}$$

| NO. | R¹ | R² | X | Y | —NR³R⁴ | Melting Point °C. | M+ |
|---|---|---|---|---|---|---|---|
| 36 | H | CH₃ | O | CH₂ | 4-phenylpiperidin-1-yl | | |
| 37 | H | OCH₃ | O | CHOH (mixed isomers) | 4-phenylpiperidin-1-yl | | |
| 38 | H | OCH₃ | O | CH₂ | 4-phenylpiperidin-1-yl | | |
| 39 | H | OCH₃ | O | CH₂ | piperidin-1-yl | | |
| 40 | H | OCH₃ | O | CH₂ | 2,6-dimethylmorpholin-4-yl | | |
| 41 | H | C₂H₅ | O | CH₂ | piperidin-1-yl | | |
| 42 | H | C₂H₅ | O | CH₂ | 2,6-dimethylmorpholin-4-yl | | |
| 43 | H | C₂H₅ | O | CH₂ | 4-phenylpiperidin-1-yl | | |
| 44 | H | i-C₃H₇ | O | CH₂ | piperidin-1-yl | | |
| 45 | H | i-C₃H₇ | O | CH₂ | 2,6-dimethylmorpholin-4-yl | | |

TABLE I-continued

[Structure: benzene ring with R¹ and R² substituents, fused to a ring containing (X) and (Y), with CH₂NR³R⁴ substituent]

| NO. | R¹ | R² | X | Y | —NR³R⁴ | Melting Point °C. | M+ |
|-----|-----|------|---|---|--------|-------------------|-----|
| 46 | H | i-C₃H₇ | O | CH₂ | —N(piperidine)-Ph (4-phenylpiperidine) | | |
| 47 | H | t-C₄H₉ | O | CHOH (Mixed isomers) | —N(piperidine) | oil | 303 |
| 48 | H | t-C₄H₉ | O | CH₂ | —N(piperidine) | oil | 287 |
| 49 | H | t-C₄H₉ | O | CHOH (Mixed isomers) | —N(2,6-dimethylmorpholine) | oil | |
| 50 | H | t-C₄H₉ | O | CH₂ | —N(2,6-dimethylmorpholine) | oil | 317 |
| 51 | H | t-C₄H₉ | O | CH₂ | —N(piperidine)-Ph (4-phenylpiperidine) | | |
| 52 | H | t-C₄H₉ | O | CH₂ | —N(piperazine)-N—Ph | | |
| 53 | H | t-C₄H₉ | O | CH₂ | —N(C₂H₅)₂ | | |
| 54 | H | t-C₄H₉ | O | CH₂ | —N(piperidine with 4-OH, 4-Ph) | | |
| 55 | OCH₃ | H | O | CHOH (mixed isomers) | —N(piperidine)-Ph (4-phenylpiperidine) | oil | 353 |
| 56 | OCH₃ | H | O | CH₂ | —N(piperidine)-Ph (4-phenylpiperidine) | oil | 337 |

TABLE I-continued

[Structure: benzene ring with R¹, R² on one side, (X) and (Y) groups connecting to CH₂NR³R⁴ side chain]

| NO. | R¹ | R² | X | Y | —NR³R⁴ | Melting Point °C. | M+ |
|---|---|---|---|---|---|---|---|
| 57 | OCH₃ | H | O | CH₂ | -N(CH(CH₃)CH₂)₂O (2,6-dimethylmorpholino) | | |
| 58 | t-C₄H₉ | H | O | CH₂ | piperidino | | |
| 59 | t-C₄H₉ | H | O | CH₂ | 2,6-dimethylmorpholino | | |
| 60 | H | F | O | CH₂ | 2,6-dimethylmorpholino | | |
| 61 | H | F | O | CH₂ | 4-phenylpiperidino | | |
| 62 | F | H | O | CH₂ | 2,6-dimethylmorpholino | | |
| 63 | F | H | O | CH₂ | 4-phenylpiperidino | | |

In the foregoing table "Ph" stands for "phenyl" ie. C₆H₅—

TABLE II

¹H nmr chemical shifts (ppm from TMS)

| Compound No. | δ (CDCl₃) |
|---|---|
| 1 | 1.15 (3H,d); 1.25 (3H,d); 1.7–2.1 and 2.4–3.0 (10H,m); 3.55–3.8 (2H,m); 4.0–4.3 (1H,m); 6.75–8.2 (4H,m). |
| 3 | 0.8 (3H,s); 0.9 (3H,s); 1.55–2.1 (8H,m); 2.5–3.0 (6H,m); 4.0–4.3 (1H,m); 6.8–7.2 (4H,m). |
| 5 | 1.65 (2H,s); 1.7–2.2 (4H,m); 2.3–3.0 (8H,m); 3.6 (1H,s); 4.0–4.3 (1H,m); 6.7–7.6 (9H,m). |
| 48 | 1.3 (9H,s); 1.4–1.6 (6H,m); 2.3–2.6 (8H,m); 2.8–2.9 (1H,m); 3.8 (1H,m); 4.3 (1H,m); 6.8–7.2 (3H,m). |
| 50 | 1.15 (3H,d); 1.2 (3H,d); 1.3 (9H,s); 1.7–18 (2H,m); 2.3 (3H,m); 2.4–2.9 (4H,m); 3.6–3.8 (2H,m); 3.8–3.9 (1H,m); 4.2–4.3 (1H,m); 6.7–6.9 and 7.0–7.2 (3H,m). |
| 56 | 1.8–1.9 (4H,m); 2.0–2.2 (2H,m); 2.3–2.6 (5H,m); 2.8–2.9 (1H,m); 3.0–3.2 (2H,m); 3.8 (3H,s); 3.8–3.9 (1H,m); 4.3–4.4 (1H,m); 6.4–6.5 (2H,m); 6.9–7.0 (1H,m); 7.2–7.4 (5H,m). |

Preferred compounds of Table I are those numbered 1, 4, 30, 48, 50 and 56.

The present invention also provides novel compounds which possess fungicidal activity and are suitable for use as the active ingredient of the compositions hereinabove defined, the compounds having one of the following formulae (II)–(V), in all of which one of $R^1$ and $R^2$ is hydrogen and the other is an iso-propyl or, preferably, a tert-butyl group:

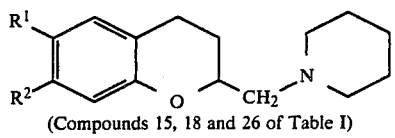

(II)

(Compounds 15, 18 and 26 of Table I)

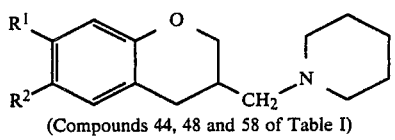

(III)

(Compounds 44, 48 and 58 of Table I)

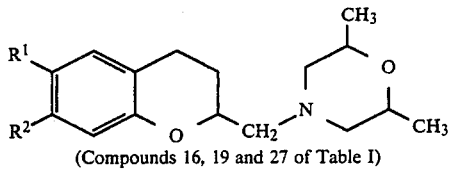

(IV)

(Compounds 16, 19 and 27 of Table I)

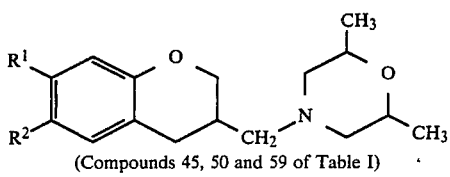

(V)

(Compounds 45, 50 and 59 of Table I)

or having one of the following formulae (VI) and (VII), in both of which one of $R^1$ and $R^2$ is hydrogen and the other is a fluorine atom or, preferably, a methoxy group:

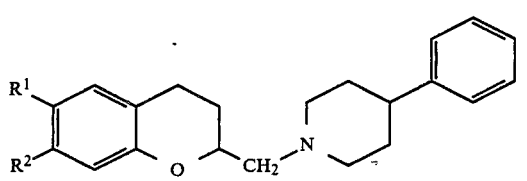

(VI)

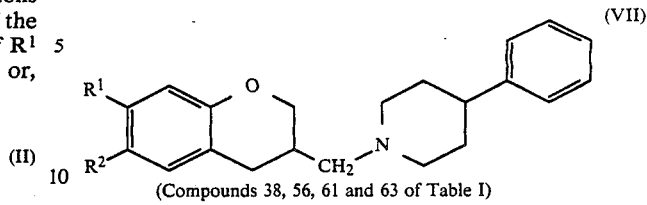

(VII)

(Compounds 11 and 25 of Table I)

(Compounds 38, 56, 61 and 63 of Table I)

Compounds of formula (I) in which X is a methylene group and Y is an oxygen atom can be prepared from the substituted phenols of general formula (XIII) by the steps shown in Scheme 1 below. Throughout Scheme 1, $R^1$, $R^2$, $R^3$ and $R^4$ are defined as above. Thus compounds of general formula (I) can be prepared by treatment of acid chlorides of general formula (VIII) with an amine of general formula (IX) in the presence of a suitable solvent such as dichloromethane and a base such as pyridine with the optional addition of a catalyst such as 4-N,N-dimethylaminopyridine, followed by reduction with a suitable reducing agent such as lithium aluminium hydride.

Compounds of general formula (VIII) can be prepared by treatment of acids of general formula (X) with a suitable chlorinating agent such as thiinyl chloride or oxalyl chloride with the optional addition of a convenient solvent such as dichloromethane.

Compounds of general formula (X) can be prepared by reduction of ketones of general formula (XI) with a suitable reducing agent, for example with zinc amalgam in the presence of hydrochloric acid, under the usual conditions of the Clemmensen reduction.

Compounds of general formula (XI) can be prepared by cyclisation of acids of general formula (XII) for example by heating with a methanolic solution of sodium acetate (see for example M Konieczny & S Korngut, Arch. Immunol. Ther. Exp. 23 (6)809 (1975)).

Compounds of general formula (XII) can be prepared by treatment of the substituted phenols of general formula (XIII) with maleic anhydride in the presence of a suitable catalyst such as aluminium chloride and a convenient solvent such as ethylene chloride at temperatures between 25° C. and 80° C. (see for example G Baddeley, S M Makar and M G Ivinson, J Chem Soc 3969 (1953)).

Scheme 1

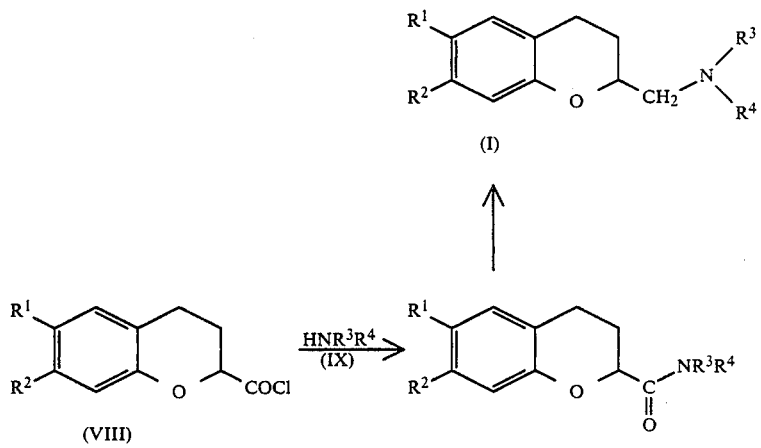

Scheme 1

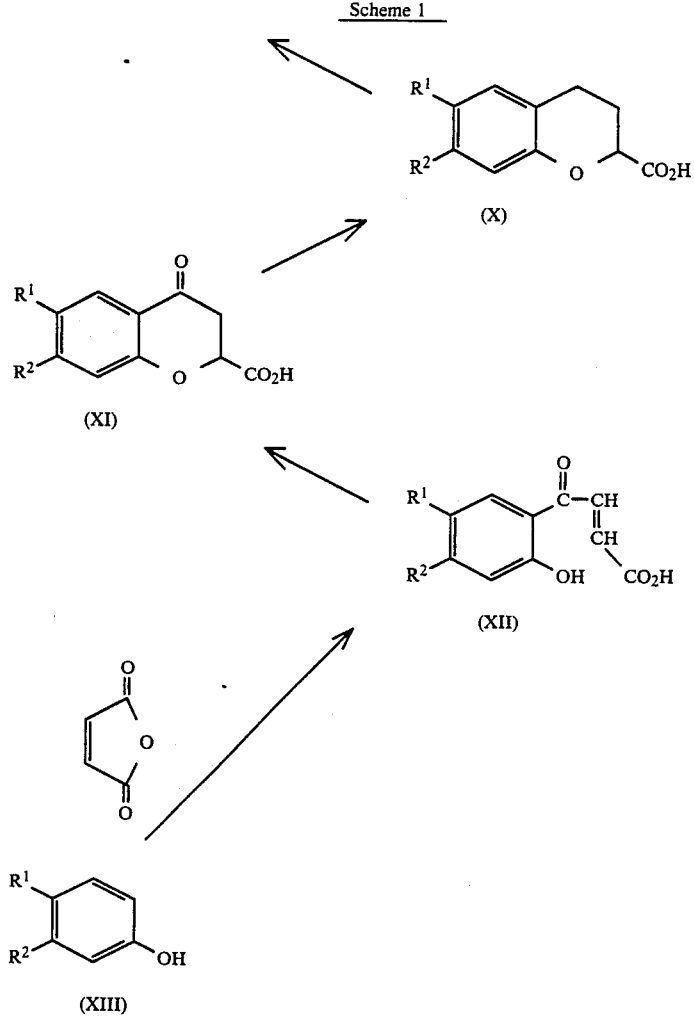

Compounds of formula (I) in which X is an oxygen atom and Y is a methylene group can be prepared from the substituted phenol of general formula (XX) by the steps shown in Scheme 2. Throughout Scheme 2, $R^1$, $R^2$, $R^3$ and $R^4$ are defined as above. Thus compounds of general formula (I) can be prepared by reduction of ketones of general formula (XIV) with a suitable reducing agent, for example with zinc amalgam in the presence of hydrochloric acid under the usual conditions of the Clemmensen reduction. Alternatively compounds of general formula (I) can be prepared by reduction of compounds of general formula (XV) by hydrogen in the presence of a suitable catalyst, for example, 10% palladium on charcoal. Compounds of general formula (XV) can be prepared by treatment of alcohols of general formula (XVI) with a suitable acid, such as dilute sulphuric acid in the absence of solvent under reflux conditions. Compounds of general formula (XVI) can be prepared by reduction of ketones of general formula (XIV) with a suitable reducing agent such as sodium borohydride in the presence of a convenient solvent such as ethanol.

Ketones of general formula (XIV) can be prepared from ketones of general formula (XVII) by treatment with an amine of general formula (IX) in a suitable solvent such as water or aqueous ethanol at temperatures between 25° C. and 80° C. Compounds of general formula (XVII) can be prepared by treatment of chromanones of general formula (XVIII) with formaldehyde and dimethylammonium chloride in the presence of an acidic catalyst under the normal conditions of the Mannich reaction.

Compounds of general formula (XVIII) can be prepared by cyclisation of phenoxypropanoic acids of general formula (XIX) in the presence of a suitable catalyst such as phosphorus pentoxide (see for example A Ricci, B Dante, N P Buu-Hoi, Ann Chim Ital 58 (4) 455 (1968)). Compounds of general formula (XIX) can be prepared from phenols of general formula (XX) by standard methods in the chemical literature.

Alternatively, compounds of general formula (XVII) can be prepared by treatment of 2-hydroxyacetophenones of general formula (XXI) with formaldehyde and dimethylammonium chloride in the presence of an acidic catalyst and using N,N-dimethylformamide as solvent at a temperature of 140°-150° C. In some cases it is possible to prepare compounds of formula (XIV) directly from 2-hydroxyacetophenones of formula (XXI) by treatment with formaldehyde and the hydrochloride of an amine of general formula (IX) under the foregoing conditions.

Compounds of general formula (XXI) can be prepared from phenols of general formula (XX) by standard methods in the chemical literature.

Scheme 2
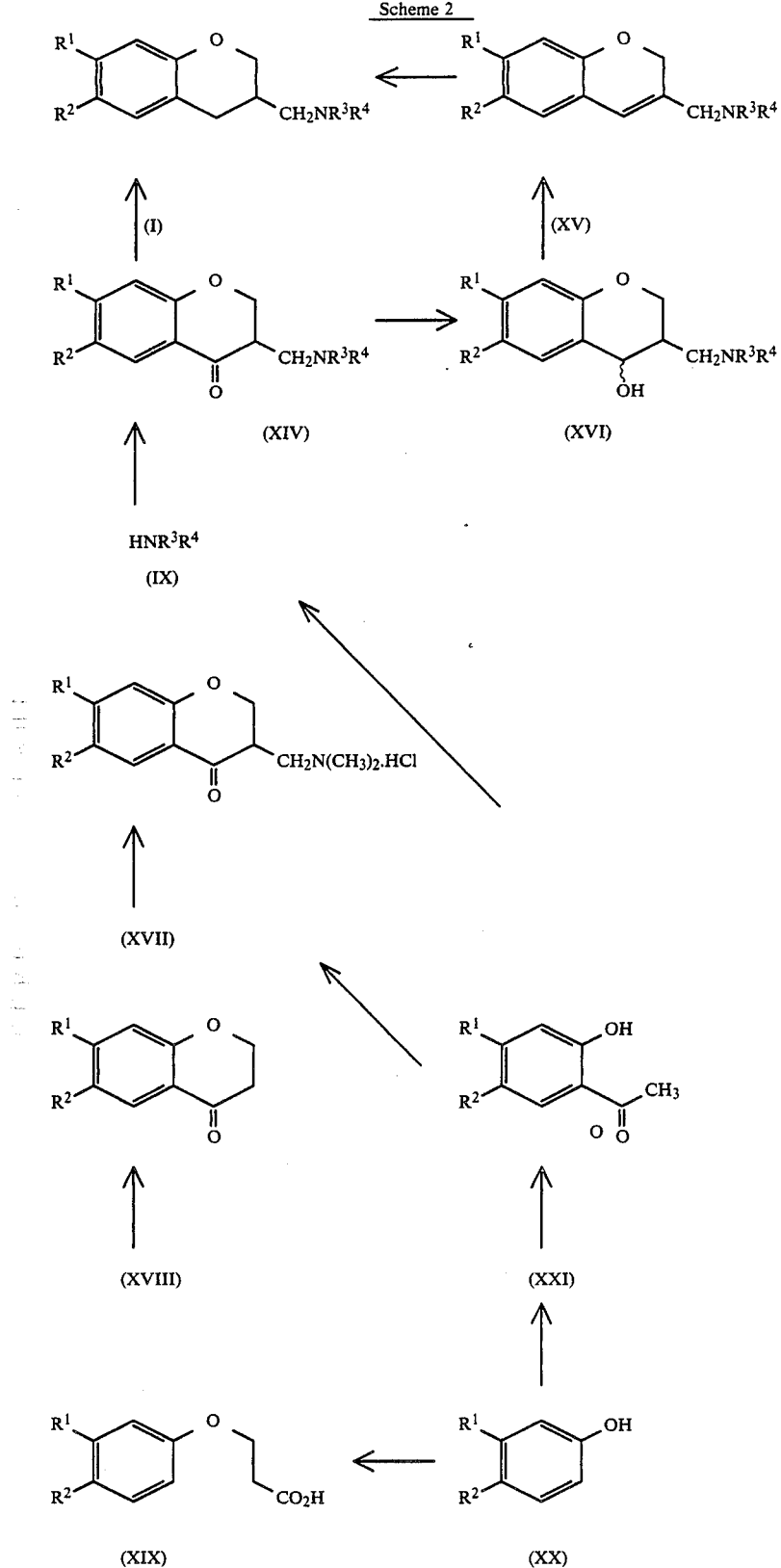
The compounds and their salts are active fungicides, particularly against the diseases:
*Puccinia recondita, Puccinia striiformis* and other rusts on wheat, *Puccinia hordei, Puccinia striiformis* and other rusts of barley, and rusts on other hosts e.g. coffee, apples, apples, vegetables and ornamental plants *Erysiphe graminis* (powdery mildew) on barley and wheat and other powdery mildews on various hosts such as *Sphaerotheca fuliginea* on cucurbits (e.g. cucumber), *Podosphaera leucotricha* on applies and *Uncinula necator* on vines Helminthosporium spp., Rhynchosporium spp. on cereals *Cercospora arachidicola* on peanuts and other Cercospora species on for example sugar beet, bananas and soya beans *Venturia inaequalis* (scab) on apples.

Some of the compounds have also shown a broad range of activities against fungi in vitro. They have activity against various post-harvest diseases on fruit (e.g. *Penicillium digatatum* and *italicum* on oranges and *Gloeosporium musarum* on bananas).

The active compounds of the invention compositions can move acropetally in the plant tissue. Moreover, the compounds can be volatile enough to be active in the vapour phase against fungi on the plant.

The invention thus provides a fungicidal or plant growth regulating composition comprising a compound of general formula (I) as hereinbefore defined, or a salt thereof, and, optionally, a carrier or diluent.

The invention also provides a method of combating fungi, which comprises applying to a plant, to seed of a plant, or to the locus of the plant or seed, a composition as hereinbefore defined.

The invention compositions can be applied directly to the foliage of a plant, to seeds, or to other medium in which plants are growing or are to be planted. They can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The compositions may also be injected into plants or sprayed onto vegetation using electrodynamic spraying techniques or other low volume methods.

The term "plant" as used herein includes seedlings, bushes and trees. Furthermore, the fungicidal methods of the invention includes preventative, protectant, prophylactic and eradicant treatment.

The type of composition used in any instance will depend upon the particular purpose envisaged.

The compositions may be in the form of dustable powders or granules comprising the active ingredient (invention compound) and a solid diluent or carrier, for example fillers such as kaolin, bentonite, kieselguhr, dolomite, calcium carbonate, talc, powdered magnesia, Fuller's earth, gypsum, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders or water dispersible granules comprising wetting or dispersing agents to facilitate their dispersion in liquids. The powders and granules may also contain fillers aand suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone and methylcyclohexanone, chlorinated hydrocarbons such as chlorobenzene and trichlorethane, and alcohols such as furfuryl alcohol, butanol and glycol ethers.

Suspension concentrates of largely insoluble solids may be prepared by ball or bead milling with a dispersing agent and including a suspending agent to stop the particles of the solid settling.

Compositions to be used as sprays may be in the form of aerosols wherein the formulation is held in a container under pressure in the presence of a propellant, e.g. fluorotrichloromethane or dichlorodifluoromethane.

The active compounds can be mixed in the dry state with a pyrotechnic mixture to form a composition suitable for generating in enclosed spaces a smoke containing the compounds.

Alternatively, the active compounds may be used in micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The active compounds can be formulated as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt thereof.

Wettable powders, emulsifiable concentrates and suspension concentrates will normally contain surfactants e.g. a wetting agent, dispersing agent, emulsifying agent or suspending agent. These agents can be cationic, anionic or non-ionic agents.

Suitable cationic agents are quaternary ammonium compounds, for example cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as olely or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use.

These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

They may also be useful as industrial (as opposed to agricultural) fungicides, eg. in the prevention of fungal attack on wood, hides, leather and especially paint films.

The compositions of this invention may contain other compounds having biological activity, eg. compounds which have similar or complementary fungicidal activity or which possess plant growth regulating, herbicidal or insecticidal activity.

Such a fungicidal compound which may be present in the composition of the invention in addition to those described herein may be one which is capable of combating ear diseases of cereals (eg. wheat) such as Rhyncosporium spp., Septoria, Gibberella and Helminthosporium spp., seed and soil borne diseases and downy and powdery mildews on grapes and powdery mildew and scab on apple etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl aluminium, fenarimol, iprodione, procymidone, vinclozolin, penconazole, myclobutanil, R0151297, S3308, pyrazophos, ethirimol, ditalimfos, tridemorph, triforine, nuarimol, triazbutyl, guazatine, propiconazole, prochloraz, flutriafol, chlortriafol ie. the chemical 1-(1,2,4-triazol-1-yl)-2-(2,4-dichlorophenyl)hexan-2-ol, DPX H6573(1-((bis-4-fluorophenyl)methylsilyl)methyl)-1H-1,2,4-triazole, triadimefon, triadimenol, diclobutrazol, fenpropimorph, fenpropidine, chlorozolinate, diniconazol, imazalil, fenfuram, carboxin, oxycarboxin, methfuroxam, dodemorph, BAS 454, mepronil, flectolanil, bitertanol, bupirimate, etaconazole, cypofuram, biloxazol, quinomethionate, dimethirimol, 1-(2-cyano-2-methoxyimino-acetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, binapacryl, nitrothalisopropyl, dodine, dithianon, fentin hydroxide, fentin acetate, tecnazene, quintozene, dichloran, copper containing compounds such as copper oxychloride, copper sulphate and Bordeaux mixture, and organomercury compounds.

The active compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (eg. grasses).

Examples of suitable plant growth regulating compounds for use with the invention compositions and compounds are the gibberellins (eg. $GA_3$, $GA_4$ or $GA_7$), the auxins (eg. indoleacetic acid, indolebutyric acid, naphthoxyacetic acid or naphthylacetic acid), the cytokinins (eg. kinetin, diphenylurea, benzimidazole, benzyladenine or benzylaminopurine), phenoxyacetic acids (eg. 2,4-D or MCPA), substituted benzoic acids (eg. triiodobenzoic acid), morphactins (eg. chlorfluoroecol), maleic hydrazide, glyphosate, glyphosine, long chain fatty alcohols and acids, dikegulac, paclobutrazol, flurprimidol, fluoridamid, mefluidide, substituted quaternary ammonium and phosphonium compounds (eg. chloromequat chlorphonium or mepiquatchloride), ethephon, carbetamide, methyl-3,6-dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (eg. bromoxynil), difenzoquat, benzoylprop-ethyl 3,6-dichloropicolinic acid, fenpentezol, inabenfide, triapenthenol and tecnazene.

The following Examples illustrate the invention; the temperatures are given in degrees Centigrade (°C.).

EXAMPLE 1

This Example illustrates the preparation of 2-[1-(4'-phenylpiperidinyl)methyl]-3,4-dihydro-1-benzopyran (Compound No. 4 in Table I) in two stages I and II.

Stage I

A solution of 3,4-dihydro-1-benzopyran-2-carboxylic acid (0.59 g 3.3 mmol) in thionyl chloride (15 ml) was stirred at 20° C. for 16 hours. Excess thionyl chloride was evaporated, azeotroping with dry toluene, to give 3,4-dihydro-1-benzopyran-2-carboxylic acid chloride as a yellow oil ($\nu$max (film) 1805 cm$^{-1}$) which was used immediately.

To a solution off the foregoing acid chloride in dry dichloromethane (5 ml) at 0° C. under $N_2$ were added dry pyridine (2 ml), N,N-dimethylaminopyridine (36 mg, 0.6 mmol) and a solution, dropwise, of 4-phenyl-piperidine (0.48 g, 3 mmol) in dry dichloromethane (10 ml). The cooling bath was removed and the mixture was stirred at 20° C. for 4 hours. Water (5 ml) was added and the solution was extracted with ethyl acetate (4×50 ml). The combined organic extracts were washed with water and brine, dried over anhydrous magnesium sulphate and concentrated in vacuo. The resulting dark orange oil was purified by column chromatography to give 2-(4'-phenylpiperidinyl)-3,4-dihydro-1-benzopyran-carboxamide (1.0 g, 100%) as a pale yellow oil having the following characteristics:

$\delta$(CDCl$_3$): 1.7–2.0 (2H, m), 2.05–2.2 (4H, m), 2.4–3.0 (4H, m), 2.9–3.3 (1H, m), 4.05–4.4 (1H, m), 4.6–4.9 (2H, m), 6.8–7.3 (9H, m).

$\nu$max (film): 3040 (m), 2950 (s), 1660 (s), 1585 (m), 1460 (s), 1220 (s), 755 (s), 700 (s) cm$^{-1}$.

m/e: 321 (M$^+$, 100%), 188 (33), 133 (42), 131 (24), 105 (54), 103 (21).

Stage II

To a suspension of lithium aluminium hydride (120 mg, 3 mmol) in dry tetrahydrofuran (20 ml) at 0° C. under nitrogen was added dropwise a solution of 3,4-dihydro-1-benzopyran-2-(4'-phenylpiperidinyl)carboxamide (480 mg, 1.5 mmol) in dry tetrahydrofuran (20 ml). The mixture was stirred at 0° C. for ½ hour and at 20° C. for 3 hours. Wet ethyl acetate (10 ml) was added dropwise then saturated sodium potassium tartrate (20 ml). After stirring for 1 hour, the mixture was extracted with ethyl acetate (4×50 ml). The combined organic extracts were washed with water and brine, dried over anhydrous magnesium sulphate and concentrated in vacuo to give a pale yellow oil. Chromatography on silica gave the title compound 2-[4'-phenylpiperidinyl)methyl]-3,4-dihydro-1-benzopyran (0.37 g, 80%) as a colourless oil having the following characteristics:

$\delta$(CDCl$_3$): 1.7–2.0 (4H, m), 2.0–2.6 (4H, m), 2.7–3.1 (4H, m), 4.2–4.7 (2H, m), 6.9–8.0 (9H, m).

$\nu$max (film): 2920 (s), 1575 (m), 1480 (m), 1450 (m), 1230 (s), 750 (s).

m/e: 307 (10%, M+), 174 (100), 131 (20), 103 (20), 91 (25).

EXAMPLE 2

This Example illustrates the preparation of trans-4-hydroxy-3-[1-(4'-phenylpiperidinyl)methyl]3,4-dihydro-1-benzopyran (Compound No. 28 in Table I) and of cis-4-hydroxy-3,4-dihydro-1-benzopyran (Compound No. 29 in Table I) in two stages, I and II.

Stage I

To a solution of 3-(N,N-dimethylaminomethyl)chroman-4-one hydrochloride (242 mg, 1 mmol) in water (40 ml) was added 4-phenylpiperidine (0.80 g, 5 mmol). The resulting suspension was stirred at 20° C. for 4 hours then extracted with chloroform (4×50 ml). The combined organic extracts were washed with water and brine, dried over anhydrous magnesium sulphate, concentrated in vacuo, and chromatographed on silica to give 3-[1-(4'-phenylpiperidinyl)methyl]chroman-4-one (300 mg, 94%) as a pale yellow oil having the following characteristics:

$\delta$(CDCl$_3$): 1.7–2.0 (4H, m), 2.0–2.6 (4H, m), 2.7–3.1 (4H, m), 4.2–4.7 (2H, m), 6.9–8.0 (9H, m).

$\nu$max (film): 2940 (s), 1700 (s), 1610 (s), 1480 (s) cm$^{-1}$.

m/e: 321 (2%, M+), 174 (100), 160 (70), 131 (35), 120 (40), 104 (25), 92 (60).

Stage II

To a solution of 3-[1-(4'-phenylpiperidinyl)methyl]chroman-4-one (0.74 g, 2.3 mmol) in methanol (10 ml) and tetrahydrofuran (10 ml) was added sodium borohydride (94 mg, 1.5 mmol). After stirring at 20° C. for 2 hours, the solvents were evaporated in vacuo and the residue was partitioned between water, adjusted to pH9 with 1M sodium hydroxide solution, and ether (50 ml). The aqueous phase was further extracted with ether (3×50 ml) and the combined organic extracts were washed with water and brine, dried over anhydrous magnesium sulphate and concentrated in vacuo. The resulting colourless oil was purified by high performance liquid chromatography to give the title compounds trans-4-hydroxy-3-[1-(4'-phenylpiperidinyl)methyl]3,4-dihydro-1-benzopyran (258 mg) and cis-4-hydroxy-3-[1-(4'-phenylpiperidinyl)methyl]3,4-dihydro-1-benzopyran 910 mg), together with mixed cis and trans isomers (200 mg) as colourless oils (total yield 578 mg, 78%), having the following characteristics:

trans isomer:

$\delta$(CDCl$_3$): 1.8–2.0 (4H, m), 2.2–2.6 (6H, m), 3.0–3.2 (1H, m), 3.3–3.5 (1H, m), 3.7–4.2 (2H, m), 3.8 (1H, d J=8.0 Hz), 6.8–7.6 (9H, m).

$\nu$max (film): 3250 (m), 2920 (s), 1600 (m), 1580 (m), 1480 (s), 1450 (s), 1220 (s), 750 (s) cm$^{-1}$.

m/e: (as SiMe$_3$ derivative): 395 (20%, M+), 233 (14), 175 (56), 174 (100), 131 (26), 115 (12), 103 (23).

cis isomer:

$\delta$(CDCl$_3$): 1.7–2.0 (4H, m), 2.0–2.9 (7H, m), 3.3–3.5 (1H, m), 4.0–4.2 (2H, m), 5.0 (1H, d J=4.9 Hz), 6.7–7.7 (9H, m).

m/e: (as SiMe$_3$ derivative): 395 (6%, M+), 174 (100), 131 (13), 103 (13).

EXAMPLE 3

This Example illustrates the preparation of 3-[1-(4'-phenylpiperidinyl)methyl]3,4-dihydro-1-benzopyran (Compound No. 30 in Table I) in two stages, I and II.

Stage I

To a mixture if cis- and trans-4-hydroxy-3-[1-(4'-phenylpiperidinyl)methyl]3,4-dihydro-1-benzopyran (0.19 g, 0.6 mmol) was added 10% aqueous sulphuric acid (10 ml). The solution was heated under reflux for 1 hour, allowed to cool, neutralised with dilute aqueous sodium hydroxide and extracted with ether (3×30 ml). The combined organic extracts were washed with saturated aqueous sodium hydrogen carbonate, water and brine, dried over anhydrous magnesium sulphate and concentrated in vacuo.

Column chromatography on silica gave 3-[1-(4'-phenylpiperidinyl)methyl]-2H-1-benzopyran (0.05 g) as a white crystalline solid having the following characteristics:

$\delta$(CDCl$_3$): 1.7–2.0 (4H, m) 2.2–2.6 (1H, m), 3.07 (2H, s), 4.8 (2H, s), 6.33 (1H, s), 6.7–7.3 (9H, m).

m/e: 305 (15%, M+), 145 (24), 144 (100), 115 (13).

Stage II

To a solution of 3-[1-(4'-phenylpiperidinyl)methyl]-2H-1-benzopyran (40 mg) in glacial acetic acid was added 10% palladium on charcoal (10 mg). The suspension was stirred under hydrogen at 30 psi for 3 hours at 20° C. The catalyst was removed by filtration through celite, washing thoroughly with ethanol. The resulting solution was concentrated in vacuo. The residue was diluted with water, neutralised with 2M aqueous sodium hydroxide and extracted with ether (4×20 ml). The combined ethereal extracts were washed with saturated aqueous sodium hydrogen carbonate (x2), water and brine, dried over anhydrous magnesium sulphate and concentrated in vacuo to give a pale yellow oil. Purification by preparative thin layer chromatography gave 3-[1-(4'-phenylpiperidinyl)methyl]3,4-dihydro-1-benzopyran (23 mg, 58%), as a colourless oil having the following characteristics:

$\delta$(CDCl$_3$): 1.7–2.0 (4H, m), 2.0–3.1 (10H, m), 3.8–4.0 (1H, m), 4.2–4.4 (1H, m), 6.8–7.4 (9H, m).

$\nu$max (film): 2940 (s), 2860 (m), 1610 (m), 1585 (s), 1490 (s), 1455 (m), 1230 (s), 755 (s), 700 (m) cm$^{-1}$.

m/e: 307 (10%, M+), 174 (100), 131 (15), 103 (15), 94 (20).

EXAMPLE 4

This Example illustrates the preparation of 4-hydroxy-3-[1-pieridinylmethyl]-6-t-butyl-3,4-dihydro-1-benzopyran (Compound 47 in Table I) in two stages, I and II.

Stage I

To a solution of 2-hydroxy-5-t-butyl-acetophenone (1.92 g, 0.01 mol) in N,N-dimethylformamide (12 ml) were added paraformaldehyde (1.1 g, 0.04 mol), piperidinium hydrochloride (4.0 g, 0.03 mol) and 12M hydrochloric acid (0.2 ml). The mixture was heated at 140°–150° C. for 90 minutes under nitrogen. The solution was cooled, diluted with water, and extracted with ether. After adjusting the pH to ca. 8, the aqueous portion was further extracted with ether. The combined organic layers were washed with water and brine, dried over anhydrous magnesium sulphate and evaporated to give a dark brown oil. This was redissolved in ether and extracted into 2M hydrochloric acid (x4). The acidic solution was neutralised and extracted with ether (x4). The ether solution was washed with water (x2) and brine, dried over anhydrous magnesium sulphate and evaporated to give a dark brown oil (1.64 g). Purification by column chromatography on silica gave 3-[1-piperidinylmethyl]-6-t-butylchroman-4-one (0.65 g) as a pale yellow oil having the following characteristics:

$\delta(CDCl_3)$: 1.3 (9H); 1.4–1.6 (6H, m); 2.2–2.4 (2H, m); 2.4–2.55 (2H, m); 2.55–2.7 (2H, m); 2.85–2.95 (1H, m); 4.4 (1H, m); 4.6 (1H, m); 6.9–6.95 (1H, m); 7.5–7.6 (1H, m); 7.9 (1H, m).

$\nu$max 2940 (s), 1690 (s), 1620 (s), 1490 (m), 1260 (m) cm$^{-1}$.

m/e 301 (2%, M+), 247 (5), 232 (5), 216 (20), 201 (100), 161 (15), 98 (60).

Stage II

To a solution of 3-[1-piperidinylmethyl]-6-t-butyl-chroman-4-one (1.18 g, 3.9 mmol) in methanol (10 ml) and tetrahydrofuran (10 ml) was added sodium borohydride (162 mg, 4.2 mmol). After stirring at 20° C. for 2½ hours, the solvents were evaporated in vacuo and the residue was partitioned between water, adjusted to ca. pH 8, and ether. The aqueous layer was further extracted with ether ($\times 3$) and the combined organic layers were washed with water ($\times 2$) and brine, dried over anhydrous magnesium sulphate and evaporated in vacuo to give a pale yellow oil (1.05 g). Chromatography on silica gave cis and trans 4-hydroxy-3-[1-piperidinylmethyl]-6-t-butyl-3,4-dihydro-1-benzopyran (0.71 g) as a colourless oil having the following characteristics:

$\delta(CDCl_3)$: 1.3 (9H, s); 1.4–1.7 (6H, m); 2.2–2.8 (7H, m); 3.7–3.8 and 4.0–4.15 (2H, m); 4.8 and 4.95 (1H, m); 6.8–6.9 (1H, m); 7.2 (1H, m); 7.5 (1H, m).

$\nu$max 3400 (s), 2950 (s), 1620 (m), 1590 (m), 1500 (s), 1460 (m), 1240 (s) cm$^{-1}$.

m/e: 303 (16%, M+) 203 (8), 177 (8), 173 (8), 98 (100).

The following are examples of compositions suitable for agricultural and horticultural purposes which can be formulated in accordance with the invention. Temperatures are given in degrees Centigrade (0° C.): percentages are by weight.

EXAMPLE 5

An emulsifiable concentrate is made up by mixing the ingredients, and stirring the mixture until all the constituents are dissolved.

| | |
|---|---|
| Compound No. 1 of Table I | 10% |
| Isophorone | 25% |
| Calcium dodecylbenzenesulphonate | 5% |
| Nonylphenolethoxylate (13 moles ethylene oxide) | 10% |
| Alkyl benzenes | 50% |

EXAMPLE 6

The active ingredient is dissolved in methylene dichloride and the resultant liquid sprayed on to the granules of attapulgite clay. The solvent is then allowed to evaporate to produce a granular composition.

| | |
|---|---|
| Compound No. 4 of Table I | 5% |
| Attapulgite granules | 95% |

EXAMPLE 7

A composition suitable for use as a seed dressing is prepared by grinding and mixing the three ingredients.

| | |
|---|---|
| Compound No. 30 of Table I | 50% |
| Mineral oil | 2% |
| China clay | 48% |

EXAMPLE 8

A dustable powder is prepared by grinding and mixing the active ingredient with talc.

| | |
|---|---|
| Compound No. 48 of Table I | 5% |
| Talc | 95% |

EXAMPLE 9

A suspension concentrate is prepared for chemicals which are largely insoluble solids by ball milling, for example, the constituents set out below, to form an aqueous suspension of the ground mixture with water.

| | |
|---|---|
| Compound No. 50 of Table I | 40% |
| Sodium lignosulphonate | 10% |
| Bentonite clay | 1% |
| Water | 49% |

This formulation can be used as a spray by diluting into water or applied directly to seed.

EXAMPLE 10

A wettable powder formulation is made by mixing together the ingredients set out below and then grinding the mixture until all are thoroughly mixed.

| | |
|---|---|
| Compound No. 58 of Table I | 25% |
| Sodium lauryl sulphate | 2% |
| Sodium lignosulphonate | 5% |
| Silica | 25% |
| China clay | 43% |

The other compounds in Table I were similarly formulated, as appropriate, depending on their physical characteristics.

EXAMPLE 11

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed on to the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease on untreated plants
The results are shown in Table III.

We claim:

1. A fungicidal composition comprising an adjuvant and/or carrier and as an active ingredient a compound having the general formula:

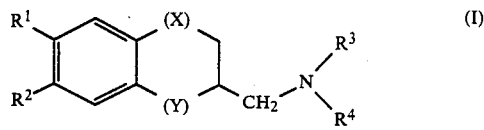

or a stereoisomer thereof, wherein X is a methylene group and Y is an oxygen atom, or X is an oxygen atom and Y is a methylene $R^1$ and $R^2$, which may be the same or different, are hydrogen or halogen atoms, or alkyl, alkenyl, alkynyl, alkoxy, haloalkyl, or haloalkoxy groups; $-NR^3R^4$ is a morpholine ring optionally substituted by alkyl, aryl, aralkyl, hydroxy, alkoxy or aryloxy groups; or an acid addition salt of such a compound.

2. A composition as claimed in claim 1, wherein in the active compound $R^1$ and/or $R^2$ are straight or branched chain alkyl groups containing from 1 to 4 carbon atoms.

3. A composition as claimed in claim 1 or claim 2, wherein in the active compound the group $-NR^3R^4$ is a morpholine or 2,6-dimethylmorpholine ring.

4. A composition as claimed in claim 1, wherein the active compound has the formula:

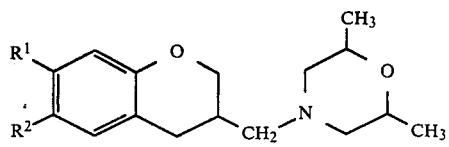

wherein one of $R^1$ and $R^2$ is hydrogen and the other is a tert-butyl group.

5. A method of combating fungi which comprises applying to a plant, to seed of a plant, or to the locus of a plant or seed, a fungicidal composition as claimed in any one of claims 1 to 3.

TABLE III

| COMPOUND NUMBER | PUCCINIA RECONDITA (WHEAT) | ERYSIPHE GRAMINIS (BARLEY) | CERCOSPORA ARACHIDICOLA (PEANUT) | VENTURIA INAEQUALIS (APPLE) |
|---|---|---|---|---|
| 1 | 0 | 4 | 0 | — |
| 3 | 0 | 3 | 0 | 0 |
| 4 | 0 | 4 | 0 | 3 |
| 5 | 0 | 3 | 0 | 0 |
| 28 | 2 | 4 | 1 | 0 |
| 29 | 0 | 4 | 0 | 0 |
| 30* | 0 | 4 | 0 | 0 |
| 47 | 0 | 4 | 0 | 0 |
| 48 | 0 | 4 | 4 | 3 |
| 50 | 1 | 0 | 4 | 4 |
| 55 | 0 | 4 | 0 | 1 |
| 56 | 3 | 4 | 4 | 0 |

*Applied at 25 ppm as a foliar spray only.